US005600017A

United States Patent [19]
Kiss et al.

[11] Patent Number: 5,600,017
[45] Date of Patent: Feb. 4, 1997

[54] DIRECT HYDROFORMYLATION OF A MULTI-COMPONENT SYNTHESIS GAS CONTAINING CARBON MONOXIDE HYDROGEN ETHYLENE AND ACETYLENE-(LAW072)

[75] Inventors: Gabor Kiss, Glenn Gardner; Michael G. Matturro, Lambertville; Harry W. Deckman, Clinton, all of N.J.; Istvan T. Horvath, New Hope, Pa.; Anthony M. Dean, Hampton, N.J.; Frank Hershkowitz, Liberty Corner, N.J.; Raymond A. Cook, Hampton, N.J.

[73] Assignee: Exxon Research and Engineering Company, Florham Park, N.J.

[21] Appl. No.: 563,838

[22] Filed: Nov. 28, 1995

Related U.S. Application Data

[63] Continuation of Ser. No. 375,324, Jan. 18, 1995, abandoned.

[51] Int. Cl.$^6$ ..................................... C07C 45/50
[52] U.S. Cl. ............................................. 568/454
[58] Field of Search ............................. 568/454

[56] References Cited

U.S. PATENT DOCUMENTS

| | | |
|---|---|---|
| 3,455,091 | 7/1969 | Herber et al. |
| 3,760,001 | 9/1973 | Staendeke |
| 4,122,123 | 10/1978 | Hestermann et al. |
| 4,210,426 | 7/1980 | Sridhar |
| 4,262,147 | 4/1981 | Garrou et al. |
| 4,593,127 | 6/1986 | Bunning et al. |
| 5,001,274 | 3/1991 | Bunning |
| 5,312,996 | 5/1994 | Packett |

OTHER PUBLICATIONS

Green et al. *Catalysis Letters* 13 (1992) 341–347. "High Yield Synthesis of Propanal from Methane and Air".
Pruett et al. *The Journal of Organic Chemistry.* 34(2) (Feb. 1969). "A Low–Pressure System for Producing Normal Aldehydes by Hydroformylation of α Olefins".
Booth et al. *Journal of Organometallic Chemistry,* 35, 195–201 (1972). "Reactions of Hydridocarbonyltris(Triphenylphosphine)–Rhodium with Alkynes".

*Primary Examiner*—Joseph Conrad
*Attorney, Agent, or Firm*—Linda M. Scuorzo

[57] ABSTRACT

The invention is a process for hydroformylating multicomponent syngas feed streams containing CO, $H_2$, $C_2$ to $C_5$ olefins and mixtures thereof and $C_2$ to $C_5$ alkynes and mixtures thereof by contacting the multicomponent syngas feed stream with a solution of an oil soluble rhodium complex catalyst produced by complexing in solution a low valence Rh and an oil soluble triorganophoshorous compound wherein the catalyst has a P/Rh ratio of at least 30, a concentration of Rh in solution from about 1 to about 1000 ppm by weight, a total concentration of coordinatively active P of at least about 0.01 mol/l, and a ratio of $[P]/p_{co}$ of at least 0.1 mmol/l/kPa, wherein [P] is the total concentration of coordinatively active phosphorous in the solution, and $p_{co}$ is the partial pressure of CO, to produce the corresponding $C_3$ to $C_6$ aldehydes. The process has utility for the hydroformylation of streams that contain olefins and alkynes.

7 Claims, 3 Drawing Sheets

DIRECT HYDROFORMYLATION OF A MULTI-COMPONENT SYNTHESIS GAS CONTAINING CARBON MONOXIDE HYDROGEN ETHYLENE AND ACETYLENE-(LAW072)

This is a continuation of application Ser. No. 08/357,324, filed Jan. 18, 1995 now abandoned.

FIELD OF THE INVENTION

This invention relates to hydroformylation methods for certain multicomponent syngas feed streams containing hydrogen, carbon monoxide, $C_2$ to $C_5$ olefins, and $C_2$ to $C_5$ alkynes.

BACKGROUND OF THE INVENTION

There is intensive research worldwide aimed at the utilization of natural gas as a petrochemical feed stock. The current use of natural gas is mainly restricted to the production of synthesis gas ("syngas", a mixture of carbon monoxide and hydrogen), and heat.

It has been long known, however, that methane can be converted to acetylene containing synthesis gas mixtures using short contact time acetylene burners. Co-producing ethylene or mixing ethylene with these acetylene rich feeds could provide a cheap, natural gas based feed stock. However, use of such coproduced feed streams has presented problems in certain processes.

Hydroformylation of highly purified olefins and syngas mixtures to aldehyde and alcohol products is well known (see B. Cornils "Hydroformylation. Oxo Synthesis, Roelen Reaction" in "New Syntheses with Carbon Monoxide", Ed. J. Falbe, Springer Verlag: New York, 1980). When pure alcohol products are desired, the aldehyde products can be hydrogenated to the corresponding alcohol derivatives. A particularly useful catalyst has been described for the hydroformylation of pure light olefin feeds as a homogeneous oil soluble phosphine modified Rh catalyst (see, e.g., U.S. Pat. Nos. 3,527,809, 3,917,661, 4,148,830) which operates at lower pressures than other homogeneous catalysts, gives high normal to iso ratios in the hydroformylation of $C_3$ and higher olefins, and has been proven to be very effective with those pure olefin feeds. The use of such an oil soluble homogeneous Rh catalyst to hydroformylate purified ethylene feeds to propanal has been also described by Evans et al (J. Chem. Soc. (A) 1968, 3133), as well as Pruett et al (J. Org. Chem. 1968, 34, 327). There is a great need, however, for a stringent purification of the feed stock, because the activity of the catalyst is strongly inhibited by acetylene and other highly unsaturated hydrocarbons if they are present as impurities in commercial oxo feeds. These components must essentially be removed before hydroformylation (see B. Cornils "Hydroformylation. Oxo Synthesis, Roelen Reaction" in "New Syntheses with Carbon Monoxide", Ed.: J. Falbe, Springer Verlag: New York, 1980, pp. 64 and 73).

Highly purified feeds of syngas (mixtures of CO and $H_2$) and olefins are currently made in two separate processes. Light olefins are usually made by steam cracking and purified by cryogenic distillation and selective hydrogenation to remove even traces of acetylenes and dienes. The currently used highly purified olefin feeds contain less than 100 ppm and typically less than 10 ppm of these impurities. In fact, a large portion of the cost of ethylene currently produced for hydroformylation by steam cracking is associated with its purification. The syngas component can be made from a hydrocarbon, such as methane or a crude distillate, and oxygen in a partial oxidation (POX) reactor run in a mode that produces essentially no dienes or acetylenes. Even though the syngas made in the POX reactor contains only trace amounts of acetylenes and dienes it is also carefully further purified before being blended with the purified olefin feed.

Hydroformylation of pure acetylenes and of pure dienes with Co or Rh catalysts is also known. (see: U.S. Pat. No. 5,312,996, 1994; P. W. N. M. Van Leeuwen and C. F. Roobeek J. Mol. Catal. 1985; U.S. Pat. No. 4,507,508, 1985; 31, 345, B. Fell, H. Bahrmann J. Mol. Catal. 1977, 2, 211; B. Fell, M. Beutler Erdöl und Kohle—Erdgas—Petrochem. 1976, 29 (4), 149; U.S. Pat. No. 3,947,503, 1976; B. Fell, W. Boll Chem. Zeit. 1975, 99(11),452; M. Orchin, W. Rupilius Catal. Rev. 1972, 6(1), 85; B. Fell, M. Beutler Tetrahedron Letters 1972, No. 33, 3455; C. K. Brown and G. Wilkinson J. Chem. Soc. (A) 1970, 2753; B. Fell, W. Rupilius Tetrahedron Letters 1969, No. 32, 2721; F. H. Jardine et al Chem. and Ind. 1965, 560; H. Greenfield et al J. Org. Chem. 1957, 22, 542; H. Adkins and J. L. R. Williams J. Org. Chem. 1952, 71, 980). The hydroformylation of these highly unsaturated compounds with cobalt catalysts is slow even at high temperatures and pressures (145°–175° C., 20–30 MPa). Furthermore, the reaction often yields side products and results in runaway reactions with sudden temperature and pressure surges. The hydroformylation of olefins is severely inhibited by acetylenes since these compounds form very stable adducts with cobalt carbonyl. Stoichiometric amounts of acetylenes can effectively transform the cobalt catalyst into these catalytically inactive acetylenic adducts (H. Greenfield et al. J. Org. Chem. 1957, 22, 542). With conventional Rh catalysts the reported reaction conditions and reaction rates are far from being practical for any commercial use. Fell typically used 17–23 MPa pressures using $PPh_3$/Rh catalyst, yet high conversions required 2 to 5 hour reaction times. Wilkinson achieved high conversion in the hydroformylation of hexyne-1 at 4.8 MPa pressure but only with a reaction time of 12 hours. Van Leeuwen and Roobeek applied conditions of 1.2 MPa, 95°–120° C., and P/Rh ratios of 10 or below in the hydroformylation of butadiene but observed low activities (orders of magnitude below that for olefins). In U.S. Pat. No. 3,947,503 a two stage process is described to hydroformylate 1,3-butadiene. In the first stage $PPh_3$/Rh catalyst is used in the presence of alcohols or diols to make the acetals of the unsaturated $C_5$-aldehyde. In the second stage this intermediate is hydroformylated using Co catalysts. The process disclosed in U.S. Pat. No. 4,507,508 also claims the conversion of conjugated dienes with organic acid or ester promoted P/Rh catalyst in the presence of alcohols. U.S. Pat. No. 5,312,996 describes a polyphosphite ligand modified Rh catalyst for the conversion of 1,3-butadiene. When using a two stage process for the hydroformylation of 1,3-butadiene with the disclosed catalyst more severe conditions are recommended in the second stage to ensure acceptable conversions. This later patent also describes 1,3-butadiene as a strong inhibitor in the conversion of alpha-olefins. In the co-conversion of alpha-olefins with 1,3-butadiene oxo aldehyde products of both the alpha-olefins and 1,3-butadiene were produced.

As mentioned, acetylenes and dienes act as strong inhibitors/poisons of catalysts in the hydroformylation of alpha-olefins and their removal is required from oxo feeds. European Patent Application No. 0225 143 A2 discloses a method for the production and utilization of acetylene and ethylene containing syngas mixtures. One of the disclosed utilization schemes is to produce propanal by hydroformylation, but acetylene first must be removed from the feed by selective hydrogenation to ethylene over a heterogeneous metal oxide or sulfide catalyst. U.S. Pat. No. 4,287,370 also teaches that inhibitors such as 1,3-butadiene must be removed from $C_4$-olefin feed stocks by selective hydrogenation prior to hydroformylation using $HRh(CO)(PPh_3)_3$ as a catalyst. German patent, DE 2638798, teaches that the removal of acetylenes and dienes is necessary in order to ensure acceptable catalyst life in the hydroformylation of olefins with a phosphine modified rhodium catalyst. In one of the most often cited sources (B. Cornils "Hydroformylation. Oxo Synthesis, Roelen Reaction" in "New Syntheses with Carbon Monoxide", Ed.: J. Falbe, Springer Verlag: New York, 1980, p. 73) acetylenes and dienes are referred to as "classical catalyst poisons" for the phosphine modified Rh oxo catalysts. Acetylenes and dienes are also reported to be strong poisons in the hydroformylation of olefins with cobalt catalysts (V. Macho and M. Polievka Rau. Roc. 1976, 18(1), 18; U.S. Pat. No. 2,752,395).

Known catalytic processes converting acetylene and ethylene containing syngas mixtures either produce products other than propanal or the conditions used and/or the reaction rates achieved are far from being practical. Thus, for example, European Patent Application No. 0,233,759 (1987) teaches the conversion of acetylene and ethylene containing syngas (a mixture of acetylene, ethylene, CO, and $H_2$ with a ratio of 6:3:30:61, respectively) into a mixture of acrylate and propionate esters in the presence of an alcohol using a Rh catalyst. When using a $PPh_3$ modified Rh oxo catalyst to convert the same feed at a P/Rh ratio of 10.6 under otherwise identical conditions, the essentially dead catalyst (turnover frequency of $1.5 \times 10^{-4}$ mol product/mol Rh/sec, and total turnover of 13 in 24 hours) described in European Patent Application No. 0,233,759 (1987) produces some propanal and acetone in a molar ratio of 90 to 1 with traces of methyl ethyl ketone and methyl propionate. It has been reported by T. Mise et al. (Chem. Lett. 1982, (3), 401) that syngas mixtures containing acetylene and ethylene yield a,b-unsaturated ethyl ketones in the presence of a Rh catalyst, however, no phosphine is present in the catalyst. Observed catalyst activities are very low, on the order of 5 turnover/h, or $1.39 \times 10^{-3}$ mol product/mol Rh/sec even though the concentration of ethylene in the gas feed is high, 41.7 v. %. The total turnover reported by Mise is only 30 in 6 hours.

Thus it would be desirable if methods could be found to enable the processing of oxo/hydroformylation feed streams using rhodium based catalysts that contain olefins and alkynes, particularly ethylene and acetylene. The present invention addresses these needs.

SUMMARY OF THE INVENTION

Figure 1:
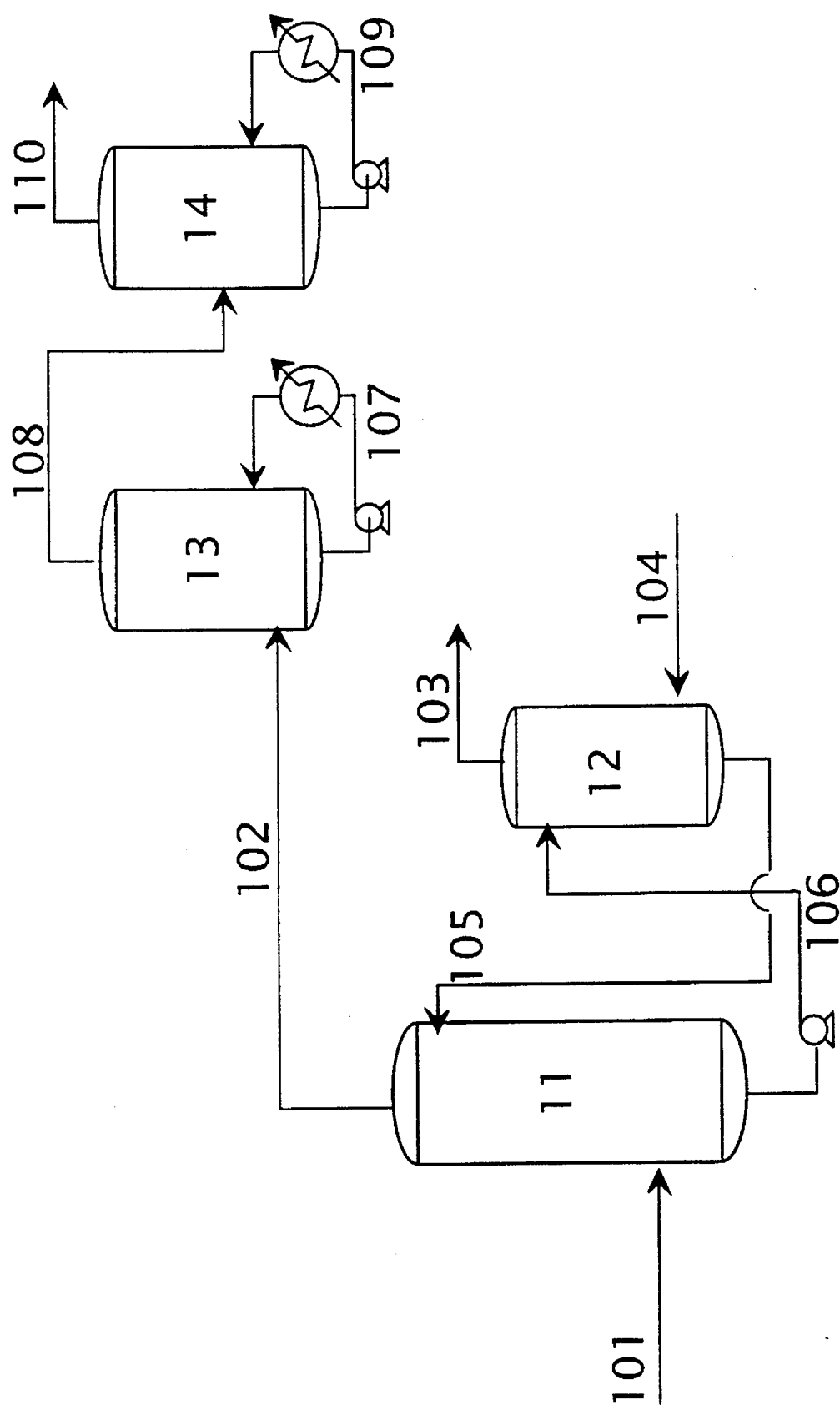
FIG. 1 describes a hydrotreating guard bed to reduce the level of multiunsaturates in a multicomponent syngas using a rhodium complex as a reagent in a scrubber guard bed.

The present invention provides for methods of using a multicomponent syngas (MCS) containing mixed unsaturated hydrocarbon feeds having both alkynes, particularly acetylene, and olefins, particularly ethylene, rather than single type feed streams, in oxo/hydroformylation reactions carried out in the presence of certain rhodium complexes as catalysts. As a benefit, the invention allows for the co-conversion of acetylene and ethylene using rhodium based catalyst technologies and provides new feed stock and processing options, and simplified production schemes for the synthesis of the corresponding product aldehydes, particularly propionaldehyde.

The present invention provides for a process for hydroformylating multicomponent syngas feed streams containing CO, $H_2$, $C_2$ to $C_5$ olefins and mixtures thereof and $C_2$ to $C_5$ alkynes and mixtures thereof, comprising: contacting a multicomponent syngas feed stream containing CO, $H_2$, and monounsaturates selected from the group consisting of $C_2$ to $C_5$ olefins and $C_2$ to $C_5$ alkynes with a solution of an oil soluble rhodium complex catalyst produced by complexing in solution a low valence Rh and an oil soluble triorganophoshorous compound wherein the catalyst has a P/Rh ratio of at least 30, a concentration of Rh in solution from about 1 to about 1000 ppm by weight, a total concentration of coordinatively active P of at least about 0.01 mol/l, and a ratio of $[P]/p_{co}$ of at least 0.1 mmol/l/kPa, wherein [P] is the total concentration of coordinatively active phosphorous in the solution, and $p_{co}$ is the partial pressure of CO, to produce the corresponding $C_3$ to $C_6$ aldehydes.

Thus, the present invention uses Rh triorganophosphorous complexes and provides for novel processes for using these complexes as catalysts to make oxygenated products comprising $C_3$ to $C_6$ aldehydes, preferably propionaldehyde (propanal), by direct hydroformylation of multicomponent synthesis gas (MCS) mixtures containing carbon monoxide, hydrogen, olefins (with a general formula of $C_nH_{2n}$ and with a functional group of C=C) having from 2 to 5 carbon atoms, alkynes (with a general formula of $C_nH_{2n-2}$ and with a functional group of C≡C) having from 2 to 5 carbon atoms. MCS mixtures can optionally contain other unsaturated hydrocarbons such as cumulated and conjugated dienes (with a general formula of $C_nH_{2n-2}$ and with a functional group of C=C=C and C=C—C=C, respectively) having 3 to 5 carbon atoms, enynes (with a general formula of $C_nH_{2n-4}$ and with a functional group of C=C=C=C) and diynes (with a general formula of $C_nH_{2n-6}$ and with a functional group of C=C=C=C) having 4 to 5 carbon atoms. MCS mixtures may also contain inert components, e.g., nitrogen, carbon dioxide, functionally inert hydrocarbons such as alkanes and aromatic hydrocarbons, and water vapor. As used herein the term "olefin" includes alkenes and excludes dienes; dienes, when present, are referred to separately. Hydroformylation of MCS mixtures is performed in the presence of catalytic amounts of oil soluble rhodium complex catalysts having a low valence Rh complexed with carbon monoxide and a triorganophosphorous ligand or a mixture of such compounds. The catalyst is contacted with the above MCS mixture in a solution of the catalyst prepared with an oily aprotic solvent or a mixture of oily aprotic solvents such as aliphatic or aromatic hydrocarbons, esters, ethers, aldehydes, the condensation side products of the product oxo aldehydes, etc.

In order to maintain the partial pressure of acetylene below the safety limit, a part of the acetylene may be scrubbed from MCS feeds before compressing them to the reaction pressure for the oxo reactor. Alternatively, the feed can be diluted with other feed components, e.g., ethylene, carbon monoxide, hydrogen or mixtures thereof as will be discussed further below. An advantage of the foregoing is that it allows for the utilization of an abundant feed stock, such as natural gas, and eliminates the need of elaborate and expensive separation and purification of oxo feeds often resulting in significant yield losses and added expense.

The present invention may suitably comprise, consist or consist essentially of the elements disclosed herein and may be practiced in the absence of any step not specifically disclosed as required.

DETAILED DESCRIPTION OF THE INVENTION

The headings herein are solely for convenience and are not intended to limit the invention in any way. In addition, solely for convenience the numbering in Figures and throughout the text is as follows: process (e.g., reactant and product) streams are numbered in hundreds, and means for carrying out a process or operation (e.g., units or devices) are numbered in tens. The first digit of each identifies the figure to which it corresponds.

The present invention pertains to processes that use multicomponent synthesis gas. A multicomponent synthesis gas (MCS) mixture is defined as gas mixtures containing carbon monoxide, hydrogen, olefins (with a general formula of $C_nH_{2n}$ and with a functional group of $C=C$) having from 2 to 5 carbon atoms, alkynes (with a general formula of $C_nH_{2n-2}$ and with a functional group of $C\equiv C$) having from 2 to 5 carbon atoms. MCS mixtures can optionally contain other unsaturated hydrocarbons such as cumulated and conjugated dienes (with a general formula of $C_nH_{2n-2}$ and with a functional group of $C=C=C$ and $C=C—C=C$, respectively) having 3 to 5 carbon atoms, enynes (with a general formula of $C_nH_{2n-4}$ and with a functional group of $C=C=C=C$) and diynes (with a general formula of $C_nH_{2n-6}$ and a functional group of $C\equiv C=C\equiv C$) having 4 to 5 carbon atoms. MCS mixtures may also contain inert components, e.g., nitrogen, carbon dioxide, functionally inert hydrocarbons such as alkanes and aromatic hydrocarbons, and water vapor.

In the following discussions "monounsaturates" are understood as a subgroup of hydrocarbon MCS components which have one unsaturated functionality that is olefins or alkynes. The "$C_2$ unsaturates" are ethylene or acetylene individually or combined. The "multiunsaturates" are a subgroup of hydrocarbon MCS components which have at least two multiple carbon-carbon bonds i.e. dienes, diynes, and enynes as defined herein, taken individually or in any combination.

The present invention provides methods for converting certain MCS feeds by reassembling its main components, hydrogen and carbon monoxide (i.e., syngas), $C_2$–$C_5$ alkynes, particularly acetylene, and $C_2$–$C_5$ olefins, particularly ethylene, by hydroformylation (oxo reaction).

One embodiment of the process of the present invention provides a method for using a multicomponent syngas feed containing at least carbon monoxide, hydrogen, and monounsaturated hydrocarbon reactants of olefinic hydrocarbons having from 2 to 5 carbon atoms (i.e. ethylene, propylene, butenes, and pentenes), and alkynes having from 2 to 5 carbon atoms (such as, e.g., acetylene and methyl acetylene), in a rhodium catalyzed low pressure oxo conversion process. These monounsaturated alkynes and olefins include the individual $C_2$–$C_5$ alkyne components and olefin components, as well as mixtures of the $C_2$–$C_5$ alkyne components and mixtures of the $C_2$–$C_5$ olefin components. In a preferred embodiment, the major monounsaturated hydrocarbon reactants are essentially ethylene and acetylene. These reactants are fed into the process as components of a multicomponent syngas which may also contain, depending on its preparation method, reactive $C_3$ to $C_5$ monounsaturates and $C_3$ to $C_5$ multiunsaturates as minor components, and functionally inert materials in varying quantities such as carbon dioxide, water vapor, nitrogen, and functionally inert hydrocarbons (such as alkanes and aromatics).

Certain trace components in the multicomponent syngas feed of the overall process referred to herein as "multicomponent process feed" are known to be detrimental in the oxo reaction. Some are irreversible catalyst poisons, e.g., sulfur compounds such as $H_2S$ and COS. Others cause reversible poisoning or accelerated catalyst deactivation. This later group includes components like halides, cyanides, oxygen, and iron carbonyls. The concentration of these detrimental components can be adjusted by a variety of techniques known in the art to provide an acceptable multicomponent syngas feed to the oxo reactor or unit referred to herein as multicomponent oxo reactor Multicomponent syngas mixtures are available from a variety of different sources. A benefit of the present invention is that any mixed acetylene-ethylene syngas mixture can be used as feed stock in the processes of the present invention.

A variety of methods exist to manufacture multicomponent synthesis gas mixtures useful in the process of the present invention. One is to blend a stream containing syngas (a mixture of CO and $H_2$) with a stream containing a mixture of acetylene, ethylene, and other unsaturated hydrocarbons. Both of these streams can be obtained from conventional petrochemical processes. The syngas (CO and $H_2$) containing stream can be produced by conventional partial oxidation (POX). Light monounsaturates ($C_2$–$C_5$) containing ethylene and acetylene as major unsaturated hydrocarbon components can be obtained from petrochemical processes such as steam cracking or acetylene manufacture, or by modification of one of the known processes used to manufacture acetylene or syngas. Thus acetylene can be formed using a partial oxidation process that applies a burner to react methane-oxygen mixtures. Acetylene burners fed with about two to one molar ratio of methane and oxygen can directly produce an acetylene rich gas mixture that contains ethylene as well as CO and hydrogen. Quenching the reaction with naphtha can further increase the concentration of acetylene and ethylene in the acetylene burner product stream. Ethylene or syngas can also be added to acetylene rich mixtures to adjust the molar ratios of the components.

Multicomponent syngas streams entering the oxo hydroformylation reactor or reaction zone (multicomponent oxo reactor feeds) in the process of the present invention contain $C_2$ to $C_5$ monounsaturates, among which the ethylene to acetylene ratio is in a range from 1:100 to 100:1, preferably 1:10 to 10:1. The amount of CO and $H_2$ in the multicomponent oxo reactor feed, with respect to the amount of monounsaturates is preferred to be at levels of at least about that required for the stoichiometric conversion of monounsaturated hydrocarbons in the oxo reaction. A stoichiometric conversion of these species requires that the mole percent of CO be equal to the sum of the mole percents of monounsaturates. Similarly, for stoichiometric conversion, the mole percent of $H_2$ should be equal to the sum of the mole percents of $C_2$ to $C_5$ olefins plus twice the mole percents of $C_2$ to $C_5$ alkynes. It is preferred that the CO and $H_2$ be present in the multicomponent oxo reactor feed in a range from half to 100 times that required for stoichiometric conversion. It is more preferred that the concentrations of CO and $H_2$ be in the range from 1 to 10 times that required for a stoichiometric conversion.

Subject to these requirements, $H_2/CO$ ratios in the multicomponent synthesis gas entering the oxo reactor (i.e. in the multicomponent oxo reactor feed) can range from 1:1 to 100:1, preferably 1:1 to 50:1, more preferably 1:1 to 10:1. While the presence of excess volumes of $H_2$ is preferred from a chemistry perspective, a large excess of $H_2$ of greater than 10 is not desirable from a materials handling perspective and can result in unnecessary expense in unit operation.

A range of composition values, as well as a typical composition for the principle species present in multicomponent syngas mixtures entering the oxo reactor (i.e. in the multicomponent oxo reactor feeds) for the process of the present invention are given in Table 1.

TABLE 1

Multicomponent oxo reactor feed compositions for the principal components

| Principal Components | Composition Range (v. %) | Typical Composition (v. %) |
|---|---|---|
| CO | 1–50 | 25 |
| $H_2$ | 1–98 | 50 |
| Ethylene | 0.1–35 | 15 |
| Acetylene | 0.1–35 | 10 |

Multicomponent syngas mixtures produced by, e.g., steam cracking or by partial oxidation can contain a variety of molecular species which are detrimental to the hydroformylation process or are known to deactivate oxo catalysts. For example, rhodium metal complex hydroformylation catalysts are known to be poisoned by certain sulfur containing molecules (e.g., $H_2S$, and COS) which irreversibly bind to the metal center. Such poisons can be removed by use of common chemical and chemical engineering techniques such as the use of guard beds, particularly guard beds containing zinc oxide.

The streams used with the present invention may also contain multiunsaturates and alkynes having 3 to 5 carbon atoms. Their concentrations are typically less than 5 volume % of the total unsaturated hydrocarbon content in the multicomponent oxo reactor ted. These highly unsaturated components, in particular the multiunsaturates, are inhibitors in the oxo conversion of olefins. They reduce the activity of the oxo catalyst by associating very strongly with the metal and blocking the activity of the catalyst toward the hydroxytrimylation of olefins. Therefore, the molar ratio of these multiunsaturates and higher alkynes to $C_2$ unsaturates should be limited as follow: alkynes having 3 to 5 carbon atoms should be limited to a level of up to 5 mole percent of the total unsaturates in the multicomponent oxo reactor ted; multiunsaturates should be limited to a level of up to 1 mole percent of total unsaturates, preferably to less than 0.1 mole percent of total unsaturates. An exception to the foregoing is the group of non-conjugated, non-cumulated dienes (diolefins), for which there are no restrictions.

Thus, generally speaking the multicomponent oxo reactor feed streams preferably contain monounsaturates. Multiunsaturated hydrocarbons containing conjugated and cumulated diene and enyne type unsaturation are considered undesirable. They should be removed from multicomponent process feeds or their concentrations should be reduced before contact with the hydroformylation catalyst. Although multicomponent syngas products generally do not require treatment before their use in the processes of the present invention, feed streams containing multiunsaturates higher than the above specified concentrations should be treated, segregated or used only after dilution with streams comprising substantially CO, $H_2$, monounsaturates, and inerts.

MULTIUNSATURATES REMOVAL

Multicomponent process feeds can be treated if necessary before entering the oxo reactor (i.e. prior to hydroformylation) if the concentration of the above specified multiunsaturated inhibiting components is too high. Mild selective hydrogenation, for example, using heterogeneous catalysts (e.g., Pd on alumina, or mixed oxide and sulfide catalysts as described in EP Application 0,225,143) can convert these reactive hydrocarbons to olefins and alkanes. These conventional heterogeneous hydrotreating methods, however, have drawbacks. For example, in heterogeneous systems high concentrations of unsaturated hydrocarbons (i.e. olefins, alkynes, and multiunsaturates) with high concentrations of hydrogen present a hazard of a highly exothermic runaway reaction. Catalyst selectivity, and other plant operation issues provide further incentives to seek alternative solutions.

Therefore, another embodiment of the present invention provides a selective, liquid phase process to address the problems associated with the application of the known heterogeneous catalysts. The liquid phase used in the process can be a homogeneous phase or a pumpable, solids-containing slurry. Applicants have found that the Rh catalyst used in the hydroformylation process of the present invention is suitable for the selective conversion of the foregoing multiunsaturated hydrocarbon components to olefins when the complex is used not as a catalyst but as a stoichiometric reagent in a separate pre-treatment step. The preferred reagent is the organophosphorous modified rhodium catalyst of the oxo/hydroformylation reactor described more detail in "Rh CATALYST/COMPLEX" below. In a preferred embodiment a two step process is used to convert excess multiunsaturates in the MCS to olefins and alkanes. In the first step of the process the Multicomponent Syngas is contacted with a solution containing the liganded rhodium complex as a reagent. The strong preferential binding of multiunsaturates to the rhodium complex serves to extract them from the MCS and into the solution where they are held as bound species on the rhodium. This gas/liquid "scrubbing" effectively removes the multiunsaturates from the MCS feed. The Rh complex essentially functions as a stoichiometric reagent, binding the multiunsaturated hydrocarbons from MCS during the contacting. In a separate, second step the multi-unsaturates are convened to the corresponding olefins and the rhodium complex is regenerated by contacting the complexed multiunsaturates containing solution with a gas of high hydrogen and low carbon monoxide content for an amount of time sufficient to effect the conversion of multiunsaturates.

If such multiunsaturates hydrogenation was carried out under conventional hydroformylation conditions, i.e. at CO partial pressures of 10–1000 kPa, the conversion of these strongly bound species to olefins would be slow (see Example 4), such that the required rhodium concentrations would be uneconomical. However, we have discovered that the conversion of these multiunsaturates can be substantially accelerated under conditions of higher hydrogen, and especially, lower CO partial pressures than conventional rhodium hydroformylation. The complexed multiunsaturates-containing Rh solution can be regenerated in a separate reactor, with a hydrogen rich gas, i.e., a gas having high hydrogen and low CO concentrations or pure hydrogen. During this regeneration, the Rh complex is returned to its multiunsaturate-free form, while the multiunsaturates are hydrogenated to the corresponding olefins and alkanes. Thus allene, for example, is hydrogenated during this process first to propylene, while butadienes are hydrogenated to butenes. In this regeneration hydrotreating step some of the olefins formed from multiunsaturates will be further hydrogenated to the corresponding alkanes. The hydrogenation rate in the regeneration step can be adjusted by adjusting the partial pressures of hydrogen and CO. Higher partial pressures of hydrogen will increase the rate of hydrogenation. On the contrary, increasing partial pressures of CO will reduce the hydrogenation activity of the catalyst. The rate and selectivity can be conveniently controlled by adjusting the partial pressure of CO in the hydrotreating reactor.

The benefit of the herein described process is that the composition of the scrubbing solution used for the stoichiometric removal of multiunsaturates can essentially be the same as used for the catalytic oxo step. Any level of multiunsaturates removal can be accomplished. The multiunsaturated hydrocarbons (e.g. allene or vinyl acetylene) are preferentially removed from the gas phase because they bind stronger than the monounsaturates, particularly olefins. Since the stronger binding components are the stronger inhibitors in the oxo conversion of monounsaturates, in particular in the oxo conversion of olefins, the process removes the strongest inhibitors first and produces a purified, multiunsaturate-deficient MCS, which is suitable as oxo/hydroformylation reactor fed. An additional advantage of using the rhodium oxo catalyst solution for the pretreatment of MCS hydroformylation feed is that it is unnecessary to rigorously control losses of rhodium complex due to entrainment in the MCS gas phase, because the downstream hydroformylation reactor system must have means to effectively capture this Rh complex. Furthermore any Rh compound carried over by the MCS stream will not contaminate the catalyst in the oxo reactor since the compositions are essentially the same.

By way of example, FIG. 1 shows Absorber 11, in which the multiunsaturates-containing MCS feed (101) is contacted with a multiunsaturates-depleted solution of the oil soluble rhodium complex (105). This absorber is analogous to guard beds of sacrificial catalyst that are sometimes used in heterogeneous catalysis. The multiunsaturates-depleted MCS stream (102) emerges from the absorber to be sent to hydroformylation (shown here as two reactors (13 and 14) in series, each with pumped around cooling (107 and 109) and reactor effluent (108 and 110). Unlike the "guard bed" of heterogeneous catalysis, the multiunsaturates-containing "sacrificial" catalyst of this process is a pumpable liquid phase solution of a Rh complex (106) that is recovered at the bottom of the absorber. The complexed multiunsaturates-containing solution (106) is pumped into a regeneration reactor (12) in which it is treated with a hydrogen-containing gas (104). In the regeneration reactor, the multiunsaturates-free rhodium complex is recovered by the hydrogenation of the complexed multiunsaturates to olefins and alkanes. A gaseous purge stream (103) from the regeneration reactor is used to preserve high concentrations of hydrogen. The regenerated, multiunsaturates-depleted solution of the Rh complex (105) is returned from the regenerator (12) to the absorber (11). To the extent that the olefin and alkane products of multiunsaturates hydrogenation remain dissolved in the catalyst solution, they will be transferred back to the MCS stream during contact with the catalyst solution in absorber (11).

The temperature in the absorber (11) is maintained in the range of 0° to 150° C., preferably between 20° to 60° C. If the temperature exceeds these limits, the Rh complex can decompose unacceptably fast. Also, at higher temperatures there is the possibility of high reactivity and exotherms if the absorber has locations where both the Rh containing solution and MCS are depleted in inhibitors. This would be true, for example, at the top of a counter-current absorber. Lower temperatures are acceptable. However, the rate of equilibration between the Rh complex and inhibitors will become limiting at some low temperatures. Furthermore, low temperatures can entail an extra cost of refrigeration with no added advantage from a process point of view. The pressure in absorber 11 is kept preferably at less than about 5 MPa with a partial pressure of acetylene below the safety limit of 0.2 MPa. In a preferred embodiment the absorber is positioned immediately before the oxo/hydroformylation reactor.

The temperature in the regenerator (12) is maintained in the range of 50° to 150° C., more preferably between 80° to 125° C. The pressure in the regenerator is typically limited by engineering, and economic factors. Higher hydrogen pressures accelerate the regeneration of the multiunsaturates-free Rh complex and the hydrogenation of the scrubbed and complexed multiunsaturates, permitting smaller regeneration vessels and smaller quantities of rhodium complex. Preferably the pressure in the regenerator is maintained in the range of about 0.1 to 50 MPa, and more preferably in the range of about 1 to 10 MPa. The liquid feed to the regenerator leaves the absorber (11) without any treatment. The gas feed is a hydrogen containing gas, which can be either essentially pure hydrogen or a gas mixture enriched in hydrogen and deficient in CO. Other guard beds designed to remove irreversible poisons of the Rh oxo catalyst such as sulfur compounds, halides, cyanides, iron carbonyls and the like, should also be used to pretreat the MCS feed stream to the multi-unsaturates absorber (11). The hydrogen-rich feed gas to the regenerator (12) should also be essentially free of the foregoing irreversible poisons, and other detrimental compounds to the Rh complex. The addition of pure, sulfur free hydrogen is preferred in the gas feed to the regenerator. The rate and selectivity of the hydrogenation step toward producing olefins from multiunsaturates and alkynes can be controlled by adjusting the partial pressure of CO. The $H_2/CO$ partial-pressure ratio in the regenerator should be 10 or higher, preferably 50 or higher. Higher CO partial pressures lead to higher selectivity to olefins but reduced rate to multi-unsaturates conversion. In certain cases the CO dissolved in the complexed multi-unsaturates-containing solution (106) can provide a sufficient partial pressure of CO in the regenerator (12). If necessary, CO can be co-fed with hydrogen containing gas into the regenerator or gas mixtures deficient in CO and enriched in hydrogen can be used.

The absence of CO does not have a destabilizing effect on the Rh complex but does affect the rate and selectivity of the hydrogenation of the unsaturated hydrocarbons present in the regenerator. With no CO present all unsaturated hydrocarbons, including olefins, tend to be hydrogenated to alkanes. It is therefore desirable to maintain CO concentration in the regenerator at a level sufficient to preferentially hydrogenate the multiunsaturates only to olefins in order to achieve an economic compromise between faster regeneration of the multiunsaturates-free Rh complex (therefore smaller equipment size, and smaller Rh load) and loss of $C_2$ to $C_5$ olefin source due to reduced selectivity. The separation of the multiunsaturates from the main stream of the multicomponent syngas improves the overall selectivity of the process since the multiunsaturates are treated separately so that the bulk of ethylene and acetylene in MCS is not exposed to the hydrogenation conditions appropriate for rapid conversion of multiunsaturates.

The flow rate of catalyst solution to the absorber is set to meet the concentration limits given for multiunsaturate of the multicomponent oxo reactor feed, as described previously. The flow rate of rhodium should be set at a sufficient level to stoichiometrically combine with the amount of multiunsaturates to be removed. Thus, a treat ratio can be defined as the ratio of the flow rate of rhodium to the absorber (expressed as moles per unit time) to the flow rate of multiunsaturates to be removed (also as moles per unit time). For an ideal absorption system, this treat ratio can be exactly 1.0 for perfect removal of only the desired multiunsaturates. Treat ratios should be between 0.5 and 50 in the current invention, preferably between 1 and 10. Higher treat ratios would be recommended if a significant fraction of the rhodium complex is inactive, or if it is desired to remove and convert some fraction of the alkyne component of the MCS in addition to the multiunsaturates.

Conditions (temperature, pressure, residence time, etc.) in the regenerator are set such that conversion rate of multiunsaturates equals the rate at which they are being carried into the regenerator by catalyst solution (which, in turn, equals the rate of multi-unsaturates removal in the absorber). Example 4 includes selected rates of multiunsaturates conversion that can be used by one skilled in the art of chemical engineering to specify operating conditions of the regenerator. The scrubbing solution may be essentially the same as that of the catalyst solution used in the oxo reactor step or any soluble or slurry phase catalyst that achieves the same effect under the conditions herein. Preferably the absorption process uses the spent catalyst solution from the oxo reactor as a scrubbing solution before its final disposal, and recycling.

An advantage of the use of the above described treatment from the aspect of the process of the present invention is that the multiunsaturates are not convened in the oxo reactor therefore do not tie up a large amount of active catalyst. They are removed from the main feed stream and separately converted into olefins. The formed olefins are then preferably recycled to the multicomponent oxo reactor feed, and hydroformylated in the oxo reactor. A further advantage of the use of the present absorption-regeneration process for multiunsaturates conversion is in the elimination of the hazard of runaway hydrogenation reactions associated with hydrogenation of highly unsaturated hydrocarbons. This hazard is eliminated in the practice of the current invention because the amount of unsaturated species in the reactor is limited to the amount carried in bound to the rhodium or physically dissolved in the solvent. Thus, each Rh site is limited to a very limited turnover before it runs out of unsaturated species to hydrogenate. Under this situation, even a rapid increase in reaction rate can only result in the conversion of a limited amount of unsaturated species and so the resulting heat release is strictly limited.

Rh OXO CATALYST

In the process of the present invention the oxo/hydroformylation catalyst is an oil soluble rhodium complex catalyst. The catalyst is formed by a complexation reaction in solution between a low valence rhodium, an oil soluble triorganophosphorous compound or a mixture of such compounds and carbon monoxide. Under reaction conditions the Rh central atom may be complexed with other species present in the reaction mixture, such as ethylene, and other olefins (e.g., propylene), acetylene, and other alkynes (e.g. methyl acetylene), dienes, and other highly unsaturated hydrocarbons (e.g., allene, butadienes, vinyl acetylene, etc.), and hydrogen which also can act as ligands.

Triorganophosphorus compounds suitable/br the preparation of the Rh complex catalyst for the use in the oxo reactor in the present invention belong to the group of oil soluble triarylphosphines, trialkylphosphines, alkyl-diarylphosphines, aryl-dialkylphosphines, trialkylphosphites, triarylphosphites, containing at least one phosphorus atom per molecule. These should be capable of complexation with Rh by the virtue of having a lone pair of electrons on the phosphorus. Non-limiting examples of such oil soluble triorganophosphorous compounds for use in the catalyst include triarylphosphines, such as triphenylphosphine or tri-p-tolylphosphine, trialkylphosphines, such as trioctylphosphine or tricyclohexylphosphine, or alkyl-diarylphosphines, such as octyldiphenylphosphine or cyclohexyldiphenylphosphine, or aryldialkylphosphines, such as phenyldioctylphosphine or phenyldicyclohexylphosphine, etc. The triorganophosphorous compounds that can serve as ligands can also be other phosphorus containing compounds such as triorganophosphites, e.g., trialkylphosphites such as trioctylphosphite, triarylphosphites such as tri-p-tolylphosphite. In addition to monodentate phosphorus ligands, bidentate compounds such as diphos (bis(diphenylphosphino)ethane) can be used An extended list of suitable phosphine ligands is given in Falbe's book at p. 55–57 incorporated herein by reference. Preferably, the oil soluble triorganophosphorous compound is a trialkylphosphine such as tricyclohexylphosphine and trioctylphosphine or a triarylphosphine such as triphenylphosphine. However, other ligands such as phenyldicyclohexylphosphine, diphenylcyclohexylphosphine, phenyldioctylphosphine, tri-p-tolylphosphine, trinaphthylphosphine, phenyl-dinaphthylphosphine, diphenyl-naphthylphosphine, tri-(p-methoxyphenyl)phosphine, tri-(p-cyanophenyl)phosphine, tri-(p-nitrophenyl)phosphine, p-N,N-dimethylaminophenyl-(diphenyl)phosphine, and the like can be used if desired. Mixtures of triorganophosphorous compounds can also be used.

Rhodium complexes prepared using the aforementioned ligands may also be used in solution in the multiunsaturates removing absorber/regenerator system described previously. In fact using the spent catalyst solution from the hydroformylation reactor before its final disposal and recycle could be advantageous because of the potential savings in reagent cost in the multiunsaturates removing step.

Rhodium complex catalysts prepared using the aforementioned ligands are known to provide good catalytic activity in the hydroformylation of pure olefin feeds but are inhibited/poisoned by alkynes, particularly acetylene. Applicants, however, have unexpectedly found that these ligands can be used in the hydroformylation of syngas containing mixed $C_2$ to $C_5$ olefin and alkyne feed stocks, especially acetylene and ethylene, provided that the P/Rh ratio in the catalyst is at least 30 or more, the total concentration of the coordinately active phosphorus is at least 0.01 mol/l or more, and the $[P]/p_{co}$ ratio in the reaction is at least 0.1 mmol/l/kPa or more. [P] is the total concentration of the coordinately active phosphorus in the solution, and $p_{co}$ is the partial pressure of carbon monoxide in the gas phase. The Rh concentration in the reaction mixture should be in the range from about $1 \times 10^{-5}$ to about $1 \times 10^{-2}$ mol/liter. This range of Rh concentrations corresponds to a Rh concentration in the range from about 1 to about 1000 ppm (by weight). In a more preferred embodiment the Rh should be present in the range of 50 to 750 ppm, based on the total weight of the solution. Within the above ranges, the choice of catalyst concentration can reflect engineering and economic considerations.

The hydroformylation of the oxo reactor feed is carried out by contacting the catalyst with the multicomponent syngas in a solution of the catalyst prepared with an oily aprotic solvent or a mixture of such solvents. Oily solvents that can be used for the preparation of the catalyst solution used in the oxo/hydroformylation step are known in the art, and include aliphatic, and aromatic hydrocarbons (e.g., heptanes, cyclohexane, toluene, etc.), esters (e.g., dioctyl phthalate), ethers, and polyethers (e.g., tetrahydrofuran, and tetraglyme), aldehydes (e.g., propionaldehyde, butyraldehyde, etc.), the aldol condensation products of the oxo product aldehydes, the triorganophosphorous ligand itself (e.g., triphenylphosphine), etc.

For catalyst compositions outside of the specified ranges, particularly for catalysts with P/Rh ratios of less than 30, the catalyst is essentially inactive. Preece and Smith (EP 0,233, 759), for example, have investigated the hydroformylation of an acetylene containing multicomponent syngas mixture in the presence of $PPh_3$ modified Rh catalyst. In spite of the fact that the feed gas contained high concentrations of the reactants (acetylene, ethylene, CO, and hydrogen with a ratio of 6:3:30:61, respectively), the catalyst solution contained high concentration of Rh (0.0108 mol/l), and $PPh_3$ (0.114 mol/l), and the total pressure was 0.91 MPa, the catalyst failed as evidenced by the fact that the total turnover, in the presence of acetylene was only 13 in 24 hours, giving a very low turnover frequency of $1.5 \times 10^{-4}$ mol propanal/mol Rh/sec. Under those reported conditions the Rh catalyst has high activity in the hydroformylation of ethylene alone (C. K. Brown, and G. Wilkinson, Tetrahedron Letters 1969, 22, 1725). Besides the expected propanal, the product mixture also contained 1.1 mol % acetone not observed in hydroformylation product mixtures of ethylene. This effect of acetylene on the oxo conversion of ethylene is well documented in the literature, and is the reason that acetylenes are referred to as "classical catalyst poisons" for the phosphine modified Rh catalysts (see B. Cornils, "Hydroformylation. Oxo Synthesis, Roelen Reaction" in *New Syntheses with Carbon Monoxide*, ed. J. Falbe, Springer Verlag, New York, 1980, p. 73).

Applicants have found, however, that under proper conditions, particularly at high P/Rh ratios the inhibiting/poisoning effect of alkynes can not only be overcome but in fact the alkyne components themselves can be converted to the corresponding saturated aldehydes. The catalyst used by applicants herein shows enhanced activity, and is not poisoned by $C_2$–$C_5$ alkynes such as acetylene but rather co-converts them with olefins to aldehydes, as evidenced by its high turnover frequency with feed streams containing acetylene, ethylene, CO, and hydrogen. Applicants have found that the catalyst system evidences changed activity with varying coordinatively active P concentrations and P/Rh ratios. Physical evidence of this change comes from experiments conducted with acetylene and ethylene containing multicomponent syngas feeds at 100° and 110° C., and 0.8 and 2.2 MPa total pressures, respectively, with different $PPh_3$/Rh ratios (see Examples 1, and 2). When the $PPh_3$/Rh ratio was 9.3, essentially the same as in the experiment of Preece and Smith, the final catalyst solution had a dark brown color but was orange when the $PPh_3$/Rh ratio was higher, e.g., 300. The brown color of the solution containing the catalyst with a P/Rh ratio of 9.3 evidenced that the catalyst decomposed and was essentially inactive. At 110° C., and 2.2 MPa total pressure the total turnover with a $PPh_3$/Rh ratio of 9.3 was only 4.9 in 2 hours, while under milder conditions of 100° C., and 0.8 MPa total pressure the total turnover was 221 in 45 minutes when the $PPh_3$/Rh ratio was 300. This later catalytic rate is in the range of the hydroformylation rate of propylene under otherwise identical conditions. The catalyst with a P/Rh ratio of 300 thus showed an average turnover frequency of 0.082 mol propanal/mol Rh/sec, while the catalyst with a P/Rh ratio of 9.3 gave an average turnover frequency of $6.8 \times 10^{-4}$ mol propanal/mol Rh/sec, i.e. 120 times slower. Initial turnover frequencies as high as 2 mol propanal/mol Rh/sec have been achieved with the process of the present invention in the conversion of an MCS fed which contained 15.5 volume % ethylene, and 6.5 volume % acetylene using a $PPh_3$/Rh catalyst with a P/Rh ratio of 660, and above (see Example 3).

Other experiments carried out with multicomponent syngas mixtures in the presence of rhodium $PPh_3$ catalysts with P/Rh ratios of 100 or higher showed high selectivity for propanal of about 99.5%, in a wide range of $H_2$/CO, and acetylene/ethylene ratios and temperatures, even at conversions as high as 99%. The only other product detected was ethane. On the other hand it has been reported (T. Mise et al. Chem. Lett. 1982, (3), 401) that acetylene and ethylene containing multi-component syngas mixtures yield $\alpha,\beta$-unsaturated ethyl ketones in the presence of unmodified Rh catalyst, where the P/Rh ratio is zero.

Applicants have found at P/Rh ratios of at least 30, and preferably above about 100, significant improvements in rate, conversion, and stability are achieved. For example, at P/Rh ratios above 30, initial rates of at least 0.04 mol/mol Rh/sec and conversions of at least 80% have been achieved with an orange-yellow catalyst color that indicates a stable catalyst. At these P/Rh ratios, the hydroformylation of acetylene and ethylene containing MCS mixtures is facilitated and also may stabilize the catalyst in a form that catalyzes hydroformylation in preference to the formation of other oxygenates, such as ketones, and esters.

Rhodium can be introduced into the reactor by methods known in the art either as a preformed catalyst, for example, a solution of hydridocarbonyl tris(triphenylphosphino) rhodium (I) [$HRh(CO)(PPh_3)_3$] or formed in situ. If the catalyst is formed in situ, the Rh can be introduced as a precursor such as acetylacetonatodicarbonyl rhodium (I) [$Rh(CO)_2(acac)$], rhodium oxide [$Rh_2O_3$], rhodium carbonyls [e.g., $Rh_4(CO)_{12}$ and $Rh_6(CO)_{16}$], tris(acetylacetonato) rhodium (I) [$Rh(acac)_3$], triarylphosphine substituted rhodium carbonyls $\{[Rh(CO)_2(PAr_3)]_2$, wherein Ar is an aryl group$\}$, etc.

REACTOR VARIABLES

In an embodiment of the process of the present invention hydroformylation of multicomponent syngas feeds is conducted in a single-stage reactor at a temperature in the range from 80° to 180° C., and preferably in the range from 80° to 155° C. If the temperature exceeds these limits, the catalyst rapidly deactivates. Lower temperatures are acceptable, however, the rate of reaction may become too slow to be economically practical.

The reaction is conducted at a total pressure in the reactor in the range of less than about 5 MPa (absolute) preferably about 0.05 to 5 MPa with a partial pressure of carbon monoxide not greater than 50% of the total pressure. The maximum practical pressure can be limited by considerations of production and capital costs, and safety.

The mole percent of carbon monoxide, hydrogen, $C_2$–$C_5$ olefins, preferably ethylene, and $C_2$–$C_5$ alkynes, preferably acetylene in the multicomponent syngas feed to the oxo reactor at the foregoing pressures should be maintained as follows: CO from about 1 to 50 mol %, probably about 1 to 35 mol %; $H_2$ from about 1 to 98 mol %, preferably about 10 to 90 mol %; monounsaturates individually and in combination from about 0.1 to 35 mol %, preferably about 1 to 35 mol %. Gas compositions within the oxo reactor in the process of the present invention are then affected by the mode of operation, feed composition, and conversion.

The reaction can be conducted either in a batch mode or on a continuous basis. Preferably the reaction is run on a continuous basis. In a continuous mode superficial velocities of from about 1.5 to about 61 cm/sec (0.05 to 2 ft/sec), preferably from about 3 to about 30 cm/sec (0.1 to 1 ft/sec) should be used.

Since the catalytic oxo conversion takes place in the liquid phase and the reactants are gaseous compounds, high contact surface between the gas and liquid phases is very desirable in order to avoid mass transfer limitations. The high contact surface can be provided by any suitable manner, for example, by stirring in a batch reactor operation. In a continuous operation the reactor feed gas can be contacted with the catalyst solution in, for example, a continuous stirred tank reactor in which the gas is introduced and dispersed at the bottom of the vessel. Good contact between the catalyst and the gas feed can also be ensured by dispersing the solution of the Rh complex catalyst on a high surface support by methods recognized in the art.

In the process of the present invention the hydroformylation of multicomponent oxo reactor feeds can also be conducted using multiple reactors in any numbers of parallel trains when operating in a continuous mode. The number of parallel trains is determined by the desired total capacity and the capacity of a single train. The present invention can be practiced using one or more stages per train, and each reaction stage can be engineered using any suitable reactor configuration. For example, plug flow or CSTR contacting are two common reactor configurations. The number of stages and the reactor types for the stages can be computed using conventional chemical engineering principals given the kinetics and objectives of the reaction system.

In the present invention, the authors have found that the olefin and alkyne contents of MCS feeds react in two well defined phases. The first phase roughly corresponds to the conversion of the olefins present in the MCS oxo reactor feed. In the second phase on the other hand mostly the alkyne content is converted. The first phase is essentially the hydroformylation of olefins in the presence of alkynes. The second phase on the other hand itself is a two step conversion in which alkynes are first hydrogenated to olefins and then those olefins formed are hydroformylated to the corresponding aldehydes. The rate determining step in this second phase of MCS conversion is the hydrogenation of alkynes to olefins. Following this unexpected order and complexity of the oxo conversion of mixed olefin-alkyne feeds, conditions for the different phases of the oxo reaction are preferably different. Thus, a preferred embodiment of the present invention is to divide the total hydroformylation into two stages, with each stage operated under conditions advantageous to the chemistry occuring in that stage. Thus reaction conditions and catalyst composition in the first reactor should enhance the hydroformylation of olefins in the presence of alkynes. Reaction conditions and catalyst composition in the second stage, on the other hand, should facilitate the hydrogenation of alkynes which is the slowest step in their conversion to aldehydes.

U.S. Pat. No. 4,593,127 describes a two stage hydroformylation process for the oxo conversion of olefins. The patent gives a common engineering solution for an improvement in the overall conversion of the reactant olefins. It has to be understood, however, that the purpose and need for a multi-stage and in particular for a two stage oxo conversion in the process of the present invention is different. The chemical reactions taking place in the different stages of the oxo process of the present invention are different. In the first oxo stage the main reaction is the hydroformylation of olefins in the presence of alkynes. In the second stage, however, the main reaction is the hydroformylation of alkynes which is itself a two stage reaction. The first step in the alkyne conversion is the hydrogenation of alkynes to the corresponding olefins which is followed by the hydroformylation of the formed olefins to the corresponding aldehydes. The chemical reaction in the two stages of the process disclosed in U.S. Pat. No. 4,593,127 on the other hand is the same: hydroformylation of olefins to aldehydes. The need for the two stages in the process of the present invention therefore does not simply stem from the need for a better overall conversion but from the unexpected nature of the chemical process, namely, that the stronger binding alkyne components react much slower than the weaker binding olefin components. As a result of this characteristics of the oxo conversion of alkyne-olefin mixtures, olefins react first producing the corresponding aldehydes and thus the alkyne reactants will be enriched in the reaction mixture. Furthermore, since the oxo conversion of alkynes to the final saturated aldehyde products requires first the hydrogenation of alkynes to the corresponding olefins and since it is this first step which determines the overall rate of this reaction, conditions in the second reactor stage should enhance in fact not only the hydroformylation of olefins but the hydrogenation of alkynes as well. The need for the second reactor stage therefore stems from the nature of the chemistry and not simply a common engineering solution to improve of the overall conversion of a chemical process.

Figure 2:
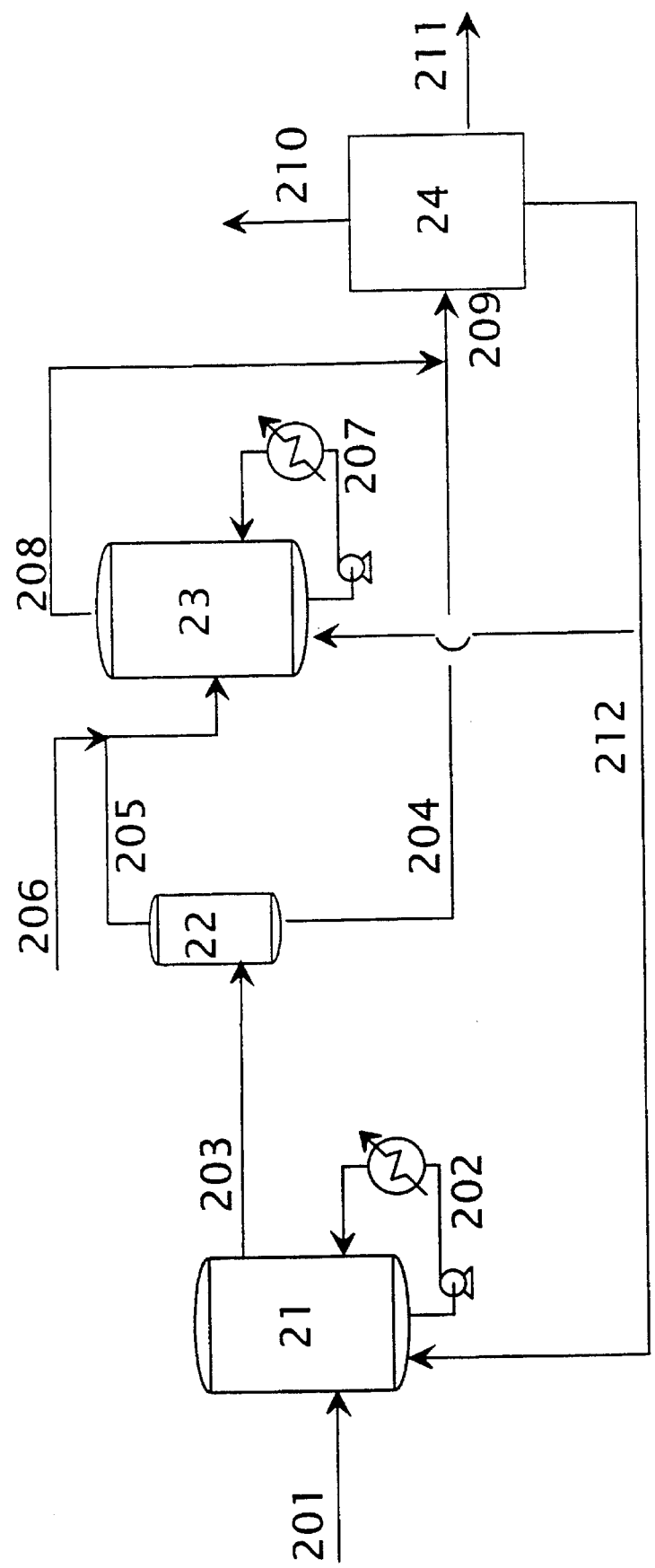
FIG. 2 describes a two-stage oxo process for the hydroformylation of multicomponent syngas mixtures.

An example of a two-stage, single-train oxo/hydroformylation unit is shown in FIG. 2 and described as follows: The hydroformylation reaction is carried out in two continuous stirred tank reactors (21, 23). Each reactor is cooled and stirred using a pump-around cooling loop (202, 207). The hydroformylation feed (201) enters the first reactor. The product from the first reactor (203), possible containing some entrained solvent and/or catalyst, may be cooled and separated in a flash drum (22) for intermediate withdrawal of aldehyde product (204). Remaining (unconverted) multicomponent syngas (205) is introduced into the second reactor (23). Additional MCS components, such as hydrogen, can be added (206) to this MCS feed to the second reactor. Hydrogen addition, for example, could be employed to provide the higher $H_2/CO$ ratios that are preferred in the second stage. The product from the second reactor (208) is combined with the intermediate product (204) to yield a stream (209) that is introduced to a product separation and catalyst recovery train (combined for simplicity into block 24). This block can use conventional boiling-point based separations (e.g. distillation) to separate the crude product into an unconverted MCS stream (210), a purified aldehyde stream (211), and a process solvent/catalyst stream (212). The process solvent and catalyst stream (212) is recycled back to the individual reactor stages.

Conditions in a two-stage oxo unit embodiment of the process of the present invention are adjusted for the two stages of the conversion of multicomponent syngas feeds as described previously. Therefore, in the preferred embodiment reaction conditions in the first stage of the two-stage oxo unit should be optimized to facilitate hydroformylation of ethylene in the presence of acetylene. In the second stage of the conversion process the overall conversion rate is essentially determined by the rate of hydrogenation of alkynes, in the preferred embodiment acetylene. Thus, reaction conditions in the second stage of a two-stage oxo unit should facilitate hydrogenation of the alkyne reactant, in the preferred embodiment acetylene. Reaction conditions in the first stage should be maintained as follows: $H_2/CO$ ratio from about 1:1 to 100:1, preferably 1:1 to 10:1; the temperature should be from about 80° to 180° C., preferably in the range of 80° to 155° C., more preferably from about 80° to 130° C. the total pressure in the reactor should be from about 0.05 to 5 MPa, preferably from about 0.1 to 2.5 MPa, with a partial pressure of CO not greater than 50% of the total pressure, and the partial pressure of acetylene reactant not greater than 0.2 MPa (satiety limit). Reaction conditions in the second stage of a two-stage oxo unit of the process of the present invention should facilitate the hydrogenation of alkynes to olefins by, for example, maintaining higher $H_2$ and lower CO partial pressures than in the first stage. Higher temperatures may also be applied in the second stage to increase reaction rates. In some cases it may become economically advantageous to use a different ligand in the second stage to improve the heat stability and/or hydrogenation activity of the catalyst. Thus reaction conditions in the second stage should be maintained as follows: $H_2/CO$ ratio from about 1:1 to 100:1, preferably from about 2:1 to 50:1; the temperature should be maintained between about 80° to 180° C., preferably from about 80° to 155° C.; the total pressure should be maintained between about 0.05 to 5 MPa, preferably from about 0.1 to 2.5 MPa, with a partial pressure of CO not greater than 35% of the total pressure, and the partial pressure of acetylene not greater than 0.2 MPa (safety limit). Superficial velocities of from about 1.5 to about 61 cm/sec (0.05 to 2 ft/sec), preferably from about 3 to about 30 cm/sec (0.1 to 1 ft/sec) should be used in both reactors in order to entrain the catalyst in the reactor. Rhodium complex catalysts within the range of compositions disclosed previously are used. The compositions of the catalyst solutions in each stage of a multistage oxo unit are preferably the same, but can also be different, within the disclosed ranges for the rhodium complex catalyst, if so desired.

The overall conversion of the alkyne and olefin content of the multicomponent syngas feed in the oxo unit of the process of present invention can be essentially as high as desired. The catalyst life, however, is shortened as the conversion approaches 100% in a single pass if higher catalyst concentrations and/or more severe conditions, i.e. higher temperatures are used to reduce the necessary residence time to achieve the desired conversion. It is therefore generally desirable to maintain the conversion in a single pass lower than the desired overall conversion and to recycle the reactants after the separation of the product. Thus, for example, higher than 99% overall conversion can be achieved with 80% per pass reactant conversion in the oxo unit and 96% reactant recovery in a recovery-recycle unit described below. Under such conditions the reactant concentration in the reactor can be 24 times higher than the concentration resulting from the same level (99%) of single pass conversion in the absence of recycle. This higher concentration contributes to a proportionally 24 times higher reaction rate, and in the case of the oxo/hydroformylation process of the present invention, it also contributes to an increased catalyst complex stability.

REACTANT RECOVERY AND RECYCLE

The use of a recycle of unreacted unsaturated hydrocarbon components is highly desirable in the processes of the present invention to increase the oxo unit productivity and the catalyst lit by allowing higher unsaturated hydrocarbon concentrations in the oxo reactor(s). However, feeds having relatively high concentrations of inerts and non-stoichiometric reactants, such as multicomponent syngas feeds, effectively discourage such a recycle because of the rapid build-up of excess gaseous materials, i.e. inerts (e.g., nitrogen, water vapor, methane, ethane, propane), and excess reactants (typically hydrogen) that would occur in the recycle loop. It would be beneficial if a process could be devised to overcome these problems.

Applicants have found that the unreacted unsaturated hydrocarbon components, especially acetylene, can be advantageously recovered from the gaseous effluent of the oxo reactor by scrubbing this "tail gas" with a liquid consisting of the liquid aldehyde product of the oxo reactor. This unsaturates-containing liquid can then either be stripped with unsaturates-free syngas to produce a recycle stream of multicomponent syngas that is more concentrated in the unsaturated hydrocarbon than was the tail gas, or preferably, the unsaturates-containing liquid can be recycled directly to the oxo reactor.

Applicants have found that solubilities of the unsaturated hydrocarbon components (e.g., ethylene, and in particular acetylene) of multicomponent syngas mixtures in certain aprotic, particularly oxygenated solvents, more particularly $C_3–C_6$ oxygenated solvents, especially the product aldehyde of the hydroformylation process such as disclosed herein for the conversion of multicomponent syngas mixtures are exceptionally high. Furthermore, the solubilities of these unsaturated hydrocarbons are substantially higher than the solubilities of other reactants such as hydrogen, and carbon monoxide, and inerts such as methane, and nitrogen (see Tables 6 and 7 in Example 5) present in multicomponent syngas mixtures used in the process of the present invention.

Thus, another embodiment of the present invention provides a process for the separation or preferential removal of unsaturated hydrocarbons, especially acetylene, from oxo reactor effluents containing same and recycle thereof into the oxo reactor for further hydroformylation processing without build-up of the aforementioned excess reactants and inerts in the oxo reactor. The process provides a method for concentrating and recovering the unsaturated hydrocarbons from the oxo reactor effluent to produce a stream that is enriched in alkyne and olefin and deficient in excess gaseous material for recycle into the oxo unit without buildup of inerts, and excess components.

The recycle and recovery concept of the present invention comprises use of the aldehyde product of hydroformylation as the absorption solvent in a system for concentrating the unconverted unsaturates in the oxo reactor effluent. A simple embodiment of this invention would be the use of paired absorption and stripping towers. In this method, the oxo effluent is fed to the bottom of an absorption tower where it is contacted with cold aldehyde to condense out liquid aldehyde and dissolve unsaturated species (particularly acetylene). Oxo tail gas greatly diminished in these components emerges from the top of the absorption tower. The unsaturates-containing aldehyde from the bottom of the absorption tower is fed to the top of a stripping tower wherein unsaturates-free gas (such as synthesis gas, hydrogen, or nitrogen) is used to strip out the unsaturates into a concentrated vapor phase suitable for recycle to oxo. The unsaturates-free liquid aldehyde product at the bottom of the stripper is divided between recycle to the absorber and a stream which is the aldehyde product of oxo. By use of such a scheme, the absorber/stripper is made to serve the three purposes: (i) recovering the aldehyde product from the gaseous process effluent, (ii) recovering unsaturates for recycle to oxo, and (iii) removal of unsaturates from the aldehyde product, in which such unsaturates would be unwanted contaminants.

Figure 3:
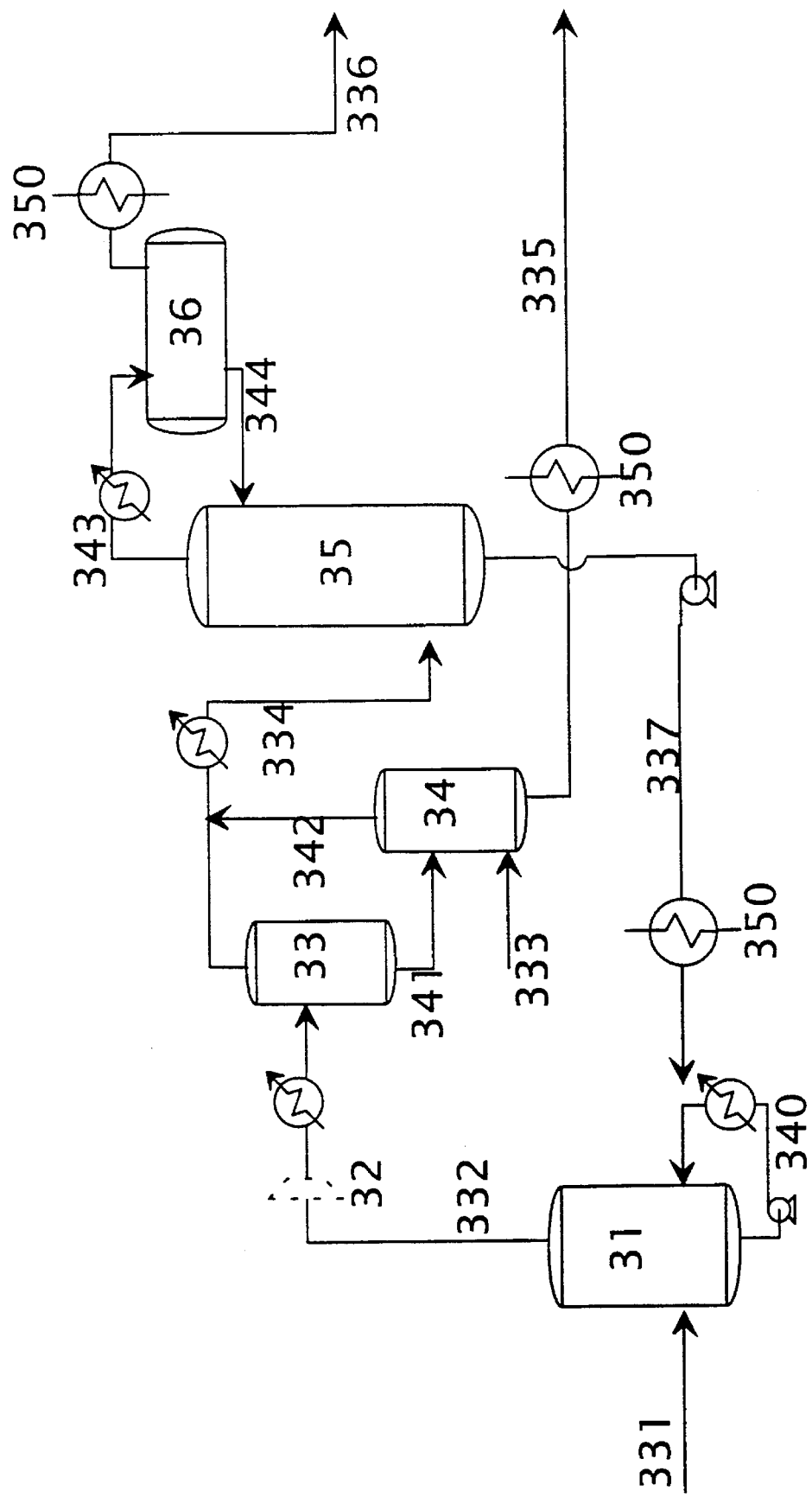
FIG. 3 describes an integrated process for aldehyde product separation and alkyne-olefin recovery with alkyne-olefin recycle.

A preferred embodiment of the recycle and recovery concept of the present invention accomplishes these same three purposes, but also provides for the recycle of the unsaturated components as solutes in a liquid-phase recycle aldehyde stream. An example flow diagram for this embodiment is shown in FIG. 3. Into the oxo reactor (31), having a pump-around cooling loop (340), is introduced a multi-component syngas feed (331). The oxo reactor gaseous or mixed phase effluent (332) is cooled to a temperature at which an amount of aldehyde condenses that is essentially equal to the amount of oxo-produced aldehyde. The condensed liquid aldehyde (341) is separated from the remaining gas phase oxo effluent in a flash drum (33). The liquid aldehyde product (341) is introduced into a stripping vessel (34) where it is stripped with an unsaturate-free gas (333) (e.g. syngas, hydrogen, nitrogen, or light alkanes) to produce an unsaturate-free aldehyde product (335) and a gaseous effluent (342) containing unsaturated hydrocarbons. The stripping tower gaseous effluent (342) is combined with the flash drum (33) vapor and cooled further to produce a stream (334) that is fed to the absorption tower (35) having an upper portion that is at a temperature sufficiently low to provide reflux (344) of the alkane components of the oxo effluent (e.g. ethane or propane) as shown as cooling of the tower overhead (343) and drum (36) to separate liquid form vapor. This upper portion of the absorber (35) functions as the rectifying section of a distillation tower, rejecting aldehyde from lower boiling components, and resulting in a substantially aldehyde-free overhead product stream (336) that contains the oxo diluents (e.g. $N_2$, methane, ethane, propane) and non-stoichiometric components (e.g. hydrogen) that boil at temperatures at or below the temperature of the refluxing alkane. In the bottom of the tower (35) the liquid phase becomes cold aldehyde that dissolves the highly soluble unsaturated components as if in an absorber. At the temperature of the bottom of the tower (35) the solubilities of alkynes and olefins in the liquid phase are very high (see Tables 5, and 6 in Example 5). For example, acetylene concentrations of 10 mol % can be achieved in the acetylene rich aldehyde product at appropriate conditions. This unsaturates-containing liquid stream (337) emerges from the bottom of the tower where it can be pumped as a liquid to substantially higher pressures for recycle to the oxo reactor (31). Once at higher pressure, the unsaturates-containing liquid stream can be heat exchanged (350) to recover any cooling value that it might contain. In this high pressure condition this heat exchange can be accomplished with a minimized concern that unsaturates such as acetylene will separate from the liquid to form a dangerous concentrated phase. Recovery of cooling value can also be employed on other cooled streams (335, 336) exiting the process.

In a further variation on this scheme, the pressure of the oxo effluent (332) can be increased in pressure prior to the recovery process via a compressor (32). The pressure increase should not increase the partial pressure of the product aldehyde over its saturation limit in order to avoid compressor damage. Furthermore, the partial pressure of acetylene at the high pressure side should be lower than the safety limit of 0.2 MPa. The increased pressure typically should not be higher than 5 MPa in order to avoid excessive equipment cost. Such a pressure increase results in an increase of the partial pressures of the components being separated: the product aldehyde and the unconverted $C_2$ to $C_5$ monounsaturates. As a result of the higher partial pressures the flash tower 33, and scrubber 35 may be operated at higher temperatures thus potentially reducing the cooling cost of the separation. Furthermore, increasing pressure can carry the added advantage of reducing tower sizes for gas treating and separations. The need and degree of this operational compression step is determined by economic and safety factors.

This recycle and recovery process is entirely different from that described in U.S. Pat. No. 3,455,091 in several ways. First, U.S. Pat. No. 3,455,091 uses high boiling oxo side-products as scrubbing solvents, versus our preferred use of the primary oxo product. Second, U.S. Pat. No. 3,455,091 uses the scrubbing system to absorb for recovery purposes the primary-product aldehyde out of the unconverted oxo feed gases, versus our absorption for recycle to oxo of selected unconverted feed components out of other feed components. This recycle and recovery process is also entirely different from that described in U.S. Pat. No. 5,001,274. While U.S. Pat. No. 5,001,274 employs a rhodium catalyst stream to absorb for recycle selected unconverted feed components, the process described herein uses the liquid reaction product. A further difference between the process of the present invention and the aforementioned prior art is that the processed stream is not the effluent of an olefin oxo unit but in fact the effluent of a different oxo technology in which olefins and alkynes are co-convened. The processed stream therefore contains chemically different components—$C_2$ to $C_5$ alkynes—in high concentration, the treatment and recovery of which requires special process conditions and technology (safety). One of the most important features of the recovery-recycle process of the present invention is that it provides a solution for the safe recovery and recycle of those alkynes, especially of acetylene.

It should be noted that this recycle and recovery process may be used with processes other than the aforementioned and herein described hydroformylation/oxo processes. The recovery and recycle process disclosed herein may be used with other synthesis processes whose reaction products are usable as absorption solvents for unreacted gaseous feed components and which synthesis process is not harmed by the recycle of said products back to the synthesis reactor. For example certain implementations of Fischer-Tropsch ("FT") synthesis can be made to produce oxygenates as products and to consume olefins in the synthesis gas feed. In such an implementation, the FT oxygenate product can be used as described herein to recover and recycle unconverted olefinic species back to the synthesis reactor. Another example is the variations of alcohol synthesis reactions that consume olefins in the synthesis gas feed and produce higher alcohol products. These are only examples and should not limit in any way the scope of application of the basic concept.

The solvent applied in the unsaturates recovery-recycle process, as it is applied to hydroformylation of multicomponent syngas, is the recovered aldehyde product from the hydroformylation of multicomponent syngas containing $C_2$–$C_5$ monounsaturates. Use of the product aldehyde as a solvent presents several advantages: the separation of the product aldehyde can be integrated into the unsaturates recovery and recycle process saving capital cost, there is reduced need for purchased solvent and solvent make-up, and reduced product contamination and solvent/product separation problems. An integrated product separation and unsaturates recovery and recycling scheme can offer further advantages relating to the need of use of refrigeration for the effective separation of the product aldehyde. Since both product separation and unsaturates recovery requires the application of low temperatures, the cooling energy can be efficiently utilized in an integrated process such as disclosed herein.

EXAMPLE 1

Apparatus

Experiments were carried out in an Autoclave Engineers' 300 ml stainless steel autoclave. The reactor was connected to a 500 ml high pressure buffer bomb through a regulator valve. Both the reactor and the buffer bomb were equipped with digital temperature and pressure gauges. The autoclave was also equipped with a temperature control unit, and a stirrer with speed control. The total and free volumes of the different pans of the apparatus were measured by gas volumetric method.

Catalyst preparation

The rhodium and phosphine containing solutions were prepared in Vacuum Atmospheres dry boxes under nitrogen or argon. The rhodium was charged either in the form of $HRh(CO)(PPh_3)_3$, or as $Rh(CO)_2(acac)$, where $PPh_3$ is triphenylphosphine, and acac is the acetylacetonato ligand. $Rh(CO)_2(acac)$ was purchased from Strem Chemicals and was used as received. $HRh(CO)(PPh_3)_3$ was prepared from $Rh(CO)_2(acac)$ by literature method (G. W. Parshall, Inorg. Synth. 1974, 15, 59). Toluene was distilled from sodium benzophenone under nitrogen. The weight of each component of the toluene solution was measured. Methylcyclohexane was used as an internal GC standard. The solution was charged under flow of nitrogen into the autoclave. The unit then was flushed with syngas ($H_2/CO=1$). When the catalyst was prepared in situ the autoclave was pressurized to about 0.5 MPa at room temperature then it was heated up to 100° C., and was kept at that temperature for about 30 min. Independent experiments demonstrated that under these conditions the rhodium looses the acac ligand by hydrogenation and the formed hydridocarbonyl triphenylphosphino rhodium complex(es) $(HRh(CO)_x(PPh_3)_y$, $x+y=4$) catalyze hydroformylation without showing any induction period. When $HRh(CO)(PPh_3)_3$ was used as a Rh source no catalyst preforming was necessary.

Hydroformylation of Gas Blend #1

The reactor containing the solution of the preformed catalyst was flushed and pressurized with Gas Blend #1 containing ethylene, ethane, acetylene, carbon dioxide, hydrogen, methane, carbon monoxide, and nitrogen (composition is given in Table 2) at room temperature. The amount of gas loaded into the reactor was determined by gas volumetric method. The P/Rh ratio in this experiment was 9.3. The composition of the catalyst charged is given in the footnote of Table 2. The reactor was heated to 110° C. and maintained at reaction temperature for two hours. While the reactor was at the reaction temperature, a pressure drop indicated that reaction occurred. After two hours at 110° C., when no further pressure drop was observed, the reactor was chilled to 15° C., and gas and liquid samples were taken. A mass balance was established for the charged materials based on GC analyses of the gas and liquid phases. The results are given in Table 2. In the liquid phase the only detected product of the reaction was identified by GC/MS as propanal. The propanal found in the liquid phase gave a 60% conversion based on the total amount of ethylene and acetylene loaded into the reactor. Since the experiment was stopped when the oxo reaction ceased the catalyst clearly deactivated before higher conversions could have been achieved. Gas analysis of the final reaction mixture indicated that both unreacted ethylene and acetylene were present at a ratio of acetylene/ethylene of 3.4 at the point when the oxo conversion stopped. The analysis results showed that a parallel conversion of both ethylene and acetylene. The final solution had a dark brown color which is associated in the experiments disclosed herein with an inactive/deactivated catalyst.

TABLE 2

Hydroformylation of Multicomponent Syngas (Gas Blend #1) at 110° C.

| Compound | x° (v. %) | n° (mmol) | n^f (mmol) | Δn (mmol) |
|---|---|---|---|---|
| $C_2H_4$ | 1.020 | 1.9 | 0.5 | −1.4 |
| $C_2H_6$ | 0.105 | 0.2 | 0.2 | 0.0 |
| $C_2H_2$ | 2.910 | 5.4 | 1.7 | −3.7 |
| $CO_2$ | 1.650 | 3.1 | 2.4 | −0.7 |
| $H_2$ | 22.310 | 41.6 | 25.5 | −16.1 |
| $CH_4$ | 4.990 | 9.3 | 8.9 | −0.4 |
| CO | 11.120 | 20.8 | 15.8 | −5.0 |
| $N_2$ | 55.895 | 116.0 | 121.6 | +5.6 |
| Propanal* | — | — | 4.4 | +4.4 |
| Total | 100.000 | 198.3 | 184.0 | −17.3 |

Reaction conditions: toluene: 90 ml, methyl cyclohexane (internal standard for GC): 0.8 ml, Rh: 897 μmoles, $PPh_3$: 8.3 mmoles, p° = 1545 kPa (at 20° C.), reaction time at 110° C.: 2 hrs.
Legend: x° = initial gas concentration, n° = initial number of mmoles in the gas phase, n^f = final number of mmoles in the gas phase, Δn = mole number change in the gas phase;
*Liquid GC results.

EXAMPLE 2

The apparatus, catalyst preparation method, and experimental procedures were the same as in Example 1. Gas Blend #2, used in this experiment, contained ethylene, ethane, acetylene, carbon dioxide, hydrogen, methane, and carbon monoxide (the composition is given in Table 3). The reaction temperature was 100° C., and the P/Rh ratio was 300. The composition of the catalyst solution is given in Table 3. After heating the reaction mixture to 100° C., a fast pressure drop in the autoclave was observed indicating that a gas consuming reaction took place. This pressure drop significantly slowed down after about 45 min reaction time when the reaction was stopped by cooling the reaction mixture to 15° C. After cooling the system gas and liquid samples were taken, and analyzed by GC. The results are given in Table 3. The analyses of both the gas and liquid phases gave a higher conversion (88.5%) at a 10° C. lower temperature, 14 times lower catalyst concentration, and in a 2.7 times shorter time than what was observed in Example 1. In addition, the color of the solution sample taken at the end of the experiment was bright orange yellow. An orange yellow color in the herein discussed experiments is associated with an active catalyst system in the conversion of acetylene and ethylene containing multi-component syngas mixtures.

TABLE 3

Hydroformylation of Multicomponent Syngas (Gas Blend #2) at 100° C.

| Compound | x° (v. %) | n° (mmol) | n^f (mmol) | Δn (mmol) |
|---|---|---|---|---|
| $C_2H_4$ | 9.91 | 9.49 | 0.77 | −8.72 |
| $C_2H_6$ | 3.26 | 3.12 | 1.69 | −1.43 |
| $C_2H_2$ | 6.83 | 6.54 | 1.08 | −5.46 |
| $CO_2$ | 2.53 | 2.42 | 1.51 | −0.91 |
| $H_2$ | 48.27 | 53.09 | 47.17 | −5.92 |
| $CH_4$ | 11.70 | 11.21 | 9.14 | −2.07 |
| CO | 17.50 | 23.32 | 8.65 | −14.67 |
| Propanal* | — | — | 14.20 | +14.20 |
| Total | 100.00 | 109.19 | 84.21 | −24.98 |

*Liquid GC result.

TABLE 3-continued

Hydroformylation of Multicomponent Syngas (Gas Blend #2) at 100° C.

| Compound | x° (v. %) | n° (mmol) | n^f (mmol) | Δn (mmol) |
| --- | --- | --- | --- | --- |

Reaction conditions: toluene: 60 ml, methyl cyclohexane (internal standard for GC): 0.8 ml, Rh: 64.3 μmoles, PPh$_3$: 19.3 mmoles, p° = 800 kPa (at 100° C.), reaction time at 100° C.: 45 min.
Legend: x° = initial gas concentration, n° = initial number of mmoles in the gas phase, n^f = final number of mmoles in the gas phase, Δn = mole number change in the gas phase;

EXAMPLE 3

This example demonstrates the effect of P/Rh ratio on the hydroformylation of acetylene and ethylene containing MCS oxo feed streams. The preparation and loading procedures of the catalyst solutions were the same as in Example 1. The solvent, tetraethylene glycol dimethyl ether (tetraglyme), was degassed before use. It also served as an internal standard in the GC analyses of the product liquid samples. The solution volume, and the total initial gas charge in each experiment was the same, 70 ml, and 95 mmoles, respectively. The apparatus was the same as in Example 1 except that a volume calibrated, high pressure injection bomb was mounted into the feed line after the high precision pressure regulator between the buffer cylinder and the autoclave. This injection bomb was used to inject known amounts of ethylene/acetylene mixtures into the autoclave. The ethylene, and acetylene charges in each experiment were around 15.4, and 6.4, respectively.

Batch kinetic experiments were carried out at constant 1 MPa total gauge pressure and 120° C. As the reaction proceeded a constant pressure was maintained by feeding syngas (CO/H$_2$=1) from the volume calibrated high pressure buffer bomb through a high precision regulator valve. The reaction was monitored by reading the pressures in the buffer (measured to an accuracy of 1 kPa) as a function of time (recorded to an accuracy of 1 second). The overall conversions of ethylene and acetylene were determined after each run by GC analyses of the liquid and gas products. The only two products of the reactions detected were propanal as major product and minor amounts of ethane. The overall conversion then was correlated to the total pressure drop and the total gas consumption in moles from the buffer bomb during the experiment. Reaction rates were calculated assuming a linear correlation between the pressure drops and conversion. Catalyst compositions, and results of seven different experiments are shown in Table 4.

TABLE 4

Effect of PPh$_3$ Concentration on the Oxo Reaction Rate and on the Conversion of Acetylene-Ethylene Mixed Feeds

| PPh$_3$ (mmoles) | Rh (μmoles) | P/Rh | Initial Rate (mol/mol Rh/sec) | Total C$_2$ Conversion (%) |
| --- | --- | --- | --- | --- |
| 0.38 | 37.8 | 10 | 0.02 | 25 |
| 1.17 | 37.7 | 31 | 0.04 | 80 |
| 4.32 | 37.7 | 115 | 0.1 | 80 |
| 8.45 | 37.4 | 226 | 0.3 | 80 |
| 16.37 | 37.6 | 435 | 0.9 | 92 |
| 23.40 | 38.0 | 660 | 2.1 | 99 |
| 30.93 | 18.8 | 1644 | 2.1 | 99 |

Solution Volume: 70 ml; H$_2$/CO = 1; Total Pressure = 1 MPa; Initital Gas Charge: 95 mmoles total, 15.4 mmoles C$_2$H$_4$, 6.4 mmoles C$_2$H$_2$, balance CO and H$_2$.

Kinetic data in Table 4 demonstrate that while the activity of the catalyst is unacceptably low at low phosphine concentrations, it increases significantly by increasing the phosphine concentration. The color of the final solutions were orange yellow, except for the run with P/Rh ratio of 10, which later was brown after 120 min reaction time. This color variation indicates that a stable catalyst system is not present at a P/Rh ratio of 10 in the hydroformylation of acetylene and ethylene containing multi-component syngas feeds. By contrast, applicants have found at P/Rh ratios of at least 30, significant improvement in rate, conversion, and stability are achieved.

EXAMPLE 4

The example demonstrates the effect of H$_2$/CO ratio on alkene (ethylene) hydroformylation in the presence of a cumulated diene (allene). The preparation and loading procedures of catalyst solutions were the same as in Example 1. The experimental method and the kinetic evaluation of experimental values were the same as in Example 3, except that 15 mmoles of ethylene was coinjected with 0.13 mmoles of allene and with different amounts of hydrogen to adjust H$_2$/CO ratios in the autoclave. The catalyst charge was 18.8 μmoles of Rh (27.7 ppm), and 8.3 mmoles of PPh$_3$ (3.1 w. %) in each experiment.

After injecting allene-ethylene mixtures into the autoclave at 120° C. the reaction first proceeded at a very slow rate. Gas analysis of the gas reaction mixture showed a slow build-up of propylene during this first slow stage of the reaction. The hydroformylation of ethylene took place only after essentially all (typically 95 to 99%) of the allene charged was convened. The length of this first phase of the reaction depended on the H$_2$/CO ratio (see Table 5).

TABLE 5

The Effect of H$_2$/CO Ratio on the Conversion Rate of Allene

| H$_2$/CO | Time Required to Convert Allene (min) | Reaction Rate (mol C$_3$H$_4$/mol Rh/min) |
| --- | --- | --- |
| 1.0 | 23 | 0.30 |
| 2.2 | 17 | 0.41 |
| 7.7 | 13 | 0.53 |
| 24.4 | 5 | 1.38 |

Solution Volume: 70 ml; H$_2$/CO = 1; Total Pressure = 1 MPa; Initial Gas Charge: 95 mmoles total, 15 mmoles C$_2$H$_4$, 0.13 mmoles C$_3$H$_4$, balance CO and H$_2$;
Rh = 27.7 ppm; [PPh$_3$] = 3.1%.

EXAMPLE 5

Gas solubilities were measured either by gas volumetric method using the same autoclave as in Example 1 or by $^1$H NMR. In the autoclave experiments the solvent was thoroughly degassed in the autoclave before the gas was charged without stirring. After a short temperature equilibration the pressure and temperature in the autoclave was recorded and then the solvent was stirred until no further pressure drop could be observed. From the known gas volume and pressure drop the amount of dissolved gas was calculated. In the $^1$H NMR. experiments either the solvent (propanal) or hexamethylbenzene served as an internal standard. The values obtained are listed in Table 6.

TABLE 6

Experimentally Determined Solubilities for Hydrogen, Carbon Monoxide, Methane, Ethylene, and Acetylene at 0.1 MPa Partial Pressure

| Solute | Solvent | Temperature (°C.) | $X_i \times 10^4$ | $C_i$ (mmol/l) | Method |
|---|---|---|---|---|---|
| Hydrogen | Tetraglyme* | 20 | 5.1 | 2.2 | autoclave |
|  |  | 100 | 7.3 | 3.0 | autoclave |
|  | $d^8$-Toluene | 22 | 3.5 | — | NMR |
| Carbon monoxide | Tetraglyme* | 20 | 11.3 | 4.9 | autoclave |
|  |  | 100 | 34.6 | 14.2 | autoclave |
| Methane | Tetraglyme* | 20 | 30.0 | 13.7 | autoclave |
|  |  | 100 | 63.0 | 26.3 | autoclave |
|  | Propionaldehyde | 22 | 23.6 | 32.7 | NMR |
| Ethylene | Tetraglyme* | 20 | 134.0 | 60.0 | autoclave |
|  |  | 100 | 76.0 | 32.6 | autoclave |
|  | Propionaldehyde | 22 | 115.0 | 159.6 | NMR |
| Acetylene | Tetraglyme* | 20 | 1224.0 | 577.0 | autoclave |
|  |  | 100 | 242.0 | 103.0 | autoclave |
|  | Toluene | 20 | 246.7 | 220.6 | autoclave |
|  |  | 100 | 178.0 | 147.7 | autoclave |
|  | Propionaldehyde | 22 | 402.0 | 557.7 | NMR |

Legend: $X_i$ = mol fraction of the gaseous component in the liquid phase; $C_i$ = molarity of the gaseous component in the liquid phase.
Note: * Tetraglyme containing 7.8 w. % $PPh_3$.

The experimentally determined (see Table 6) and literature values (see Table 7) reflect high solubilities of ethylene and acetylene in oxygenates, especially in propanal. There is a large difference in solubility between ethylene and acetylene vs. all other major components of typical multicomponent syngas mixtures such as hydrogen, carbon monoxide, and methane. It can also be seen that the solubility difference increases with decreasing temperature.

TABLE 7

Gas Solubilities in Oxygenate Solvents

| Solute | Solvent | Temperature (°C.) | $X_i \times 10^4$ | $C_i$ (mmol/l) | Ref.* |
|---|---|---|---|---|---|
| Hydrogen | 2-Methylbutanal | 30 | 8.55 | — | e |
|  | 2-Methylbutanal | 100 | 11.45 | — | e |
|  | Formaldehyde diethyl acetal | 30 | 5.37 | 5.07 | g |
|  | Propionaldehyde | 100 | 5.95 | — | k |
|  | Methyl acetate | 18 | 2.51 | 3.30 | l |
|  | Ethyl acetate | 18 | 3.46 | 3.84 | l |
|  | 1-Propyl acetate | 18 | 4.15 | 3.99 | l |
|  | 2-Propyl acetate | 18 | 4.83 | 4.64 | l |
|  | 1-Butyl acetate | 18 | 4.29 | 3.64 | l |
|  | Methyl propanoate | 18 | 3.77 | 4.19 | l |
|  | Methyl butanoate | 18 | 4.67 | 4.49 | l |
|  | Ethylene glycol dimethyl ether | 100 | 6.20 | 5.32 | t |
|  |  | 100 | 6.58 | 3.89 | v |
|  | 2-Ethylhexanol-1 | 100 | 5.85 | 3.45 | w |
|  | 2-Ethylhexanol-1 2-Ethylhexanal-1 | 100 | 5.97 | — | v |
| Carbon monoxide | 2-Methylbutanal | 30 | 10.96 | — | e |
|  | 2-Methylbutanal | 100 | 13.93 | — | e |
| Methane | Formaldehyde diethyl acetal | 30 | 37.40 | 35.28 | g |
|  | Propionaldehyde | 100 | 20.90 | — | k |
| Ethylene | Formaldehyde diethyl acetal | 30 | 185.00 | 174.53 | g |
| Ethane | Formaldehyde diethyl acetal | 30 | 214.00 | 201.89 | g |

Legend: $X_i$ = mol fraction of the gaseous component in the liquid phase; $C_i$ = molarity of the gaseous component in the liquid phase.
*Table 7 References:
e) R. A. Aronovich, I. I. Vasil'eva, S. M. Loktev, A. A. Polyakov, E. V. Slivinskii, T. N. Tyvina Teor. Eksp. Khim. 1991, 27(2), 241.
g) L. P. Lizano, M. C. Lopez, F. M. Royo, J. S. Urieta J. Solution Chem. 1990, 19(7), 721.
k) I. I. Vasil'eva, A. A. Naumova, A. A. Polyakov, T. N. Tyvina, V. V. Fokina Zh. Prikl. Khim. 1987, 60(2), 408.
t) E. Brunner J. Chem. Thermodynamics 1980, 12, 993.
v) N. G. Raginskaya, N. G. Tyurikova, N. L. Nechitailo Khim. Prom-st. 1979, 1, 21.
w) E. Brunner Ber. Bunsenges. Phys. Chem. 79, 83(7), 715.

EXAMPLE 6

The preparation and loading procedures of catalyst solutions were the same as in Example 1. The experimental method and the kinetic evaluation of experimental values were the same as in Example 3, except that 15 mmoles of ethylene was coinjected with 0.13 mmoles of one of the following dienes or acetylenes: 1,3-butadiene, allene, propyne, and acetylene. The catalyst charge was 18.8 mmoles of Rh (27.7 ppm), and 8.3 mmoles of $PPh_3$ (3.1 w. %) in each experiment.

Gas analysis of the gas reaction mixtures indicated a parallel conversion of ethylene with 1,3-butadiene, propyne, and acetylene. In the case of ethylene-allene mixtures, however, the conversion of ethylene could only start after essentially all the allene injected had been hydrogenated to propylene, as disclosed in Example 4. The final reaction mixtures contained essentially propanal, ethane, and the hydrogenated product of the coinjected highly unsaturated component. Thus 1,3-butadiene yielded butenes, and allene and propyne yielded propylene. At 95 to 98% ethylene conversion the typical conversions of 1,3-butadiene, and propyne to the corresponding olefins were ca. 60%. Since the hydrogenation product of acetylene is ethylene its intermediacy could not be detected in the hydroformylation of ethylene-acetylene mixtures. The observed reaction rates showed a different degree of inhibition on the oxo rate of ethylene by the highly unsaturated component. Thus, the observed turnover frequencies in ethylene hydroformylation with allene, 1,3-butadiene, propyne, and acetylene as coinjected reactants at 33% ethylene conversion were 3, 5.5, 7, and 9 mol propanal/mol Rh/sec, respectively.

What is claimed is:

1. A process for hydroformylating multicomponent syngas feed streams containing CO, $H_2$, $C_2$ to $C_5$ olefins and mixtures thereof and $C_2$ to $C_5$ alkynes and mixtures thereof, comprising: contacting the multicomponent syngas feed stream containing CO, $H_2$, monounsaturated olefins selected from the group consisting of $C_2$ to $C_5$ olefins and mixtures thereof and monounsaturated alkynes selected from the group consisting of $C_2$ to $C_5$ alkynes and mixtures thereof with a solution of an oil soluble rhodium complex catalyst produced by complexing in solution a low valence Rh and an oil soluble triorganophoshorous compound wherein the catalyst has a P/Rh ratio of at least 30, a concentration of Rh in solution from about 1 to about 1000 ppm by weight, a total concentration of coordinatively active P of at least about 0.01 mol/l, and a ratio of $[P]/p_{co}$ of at least 0.1 mmol/l/kPa, wherein [P] is the total concentration of coordinatively active phosphorous in the solution, and $p_{co}$ is the partial pressure of CO, to produce the corresponding $C_3$ to $C_6$ aldehydes.

2. The process of claim 1 wherein the olefin is essentially ethylene, the alkyne is essentially acetylene, and the aldehyde product is propanal.

3. The process of claim 1 wherein the partial pressure ratio of $H_2$/CO is from 1 to 100, the partial pressure ratio of CO/monounsaturates is from 0.5 to 100, and of $H_2$/monounsaturates is from 0.5 to 100.

4. The process of claim 1 wherein the oil soluble triorganophosphorous ligand is selected from the group consisting of oil soluble triarylphosphines, trialkylphosphines, alkyl-diaryl phosphines, aryl-dialkylphosphines, trialkylphosphites, and triarylphosphites having at least one phosphorus atom per molecule.

5. The process of claim 1 wherein the reaction temperature is from about 80° C. to about 180° C., the total pressure from about 0.05 to about 5 MPa, the partial pressure of carbon monoxide up to 50 mol % of the total pressure, the mole % of $H_2$ is from about 1 to about 98 mole %, and mol % of ethylene and acetylene each alone and in combination is from about 0.1 to about 35 mol %.

6. The process of claim 1 wherein the contacting is carried out in at least two reactor stages.

7. The process of claim 1 wherein the contacting is carried out in two stages, wherein the first stage is optimized at conditions for conversion of olefins in the presence of alkynes, and the second stage is optimized at hydrogenation conditions for conversion of alkynes to olefins.

* * * * *